US00PP19417P3

(12) United States Plant Patent
Bremer

(10) Patent No.: US PP19,417 P3
(45) Date of Patent: Nov. 4, 2008

(54) ***CORTADERIA* PLANT NAMED 'AMCO'**

(50) Latin Name: *Cortaderia selloana*
Varietal Denomination: Amco

(76) Inventor: Hinrich Bremer, Omorikastrasse 5, D-26655 Westerstede (DE)

( * ) Notice: Subject to any disclaimer, the term of this patent is extended or adjusted under 35 U.S.C. 154(b) by 0 days.

(21) Appl. No.: 11/702,826

(22) Filed: Feb. 6, 2007

(65) Prior Publication Data

US 2008/0196133 P1 Aug. 14, 2008

(51) Int. Cl.
*A01H 5/00* (2006.01)

(52) U.S. Cl. ..... Plt./384

(58) Field of Classification Search ..... Plt./384
See application file for complete search history.

*Primary Examiner*—Kent L. Bell

*Assistant Examiner*—Georgia Helmer

(74) *Attorney, Agent, or Firm*—The Webb Law Firm

(57) ABSTRACT

A new and distinct *Cortaderia* plant having variegated foliage and a long flowering season.

5 Drawing Sheets

Botanical classification: *Cortaderia selloana.*
Varietal denomination: 'Amco'.

BACKGROUND OF THE INVENTION

The present invention comprises a new and distinct cultivar of *Cortaderia* plant (Pampas grass) known by the varietal name 'Amco'. The new variety was discovered in 1998 as a selected mutation in Germany. The new variety was first asexually reproduced in 1999 by vegetative division in Germany. The new variety has been found to retain its distinctive characteristics and remain true to type through successive propagations.

'Amco' has white inflorescences, variegated foliage, and lacks seed production like *Cortaderia* variety 'Splendid Star' (U.S. Plant Pat. No. 16,277). However, 'Splendid Star' exhibits greenish-gold leaf variegation and 'Amco' exhibits a larger growth habit and only female sexual characteristics.

The following traits also distinguish 'Amco' as a new and distinct cultivar from other *Cortaderia* varieties known to the breeder:

1. Variegated foliage (white stripes on leaf blades);
2. Growth habit; and
3. Lacks male sexual characteristics.

DESCRIPTION OF THE DRAWINGS

The accompanying photographic drawings illustrate the new variety, with the color being as nearly true as is possible with color illustrations of this type.

Figure 1:
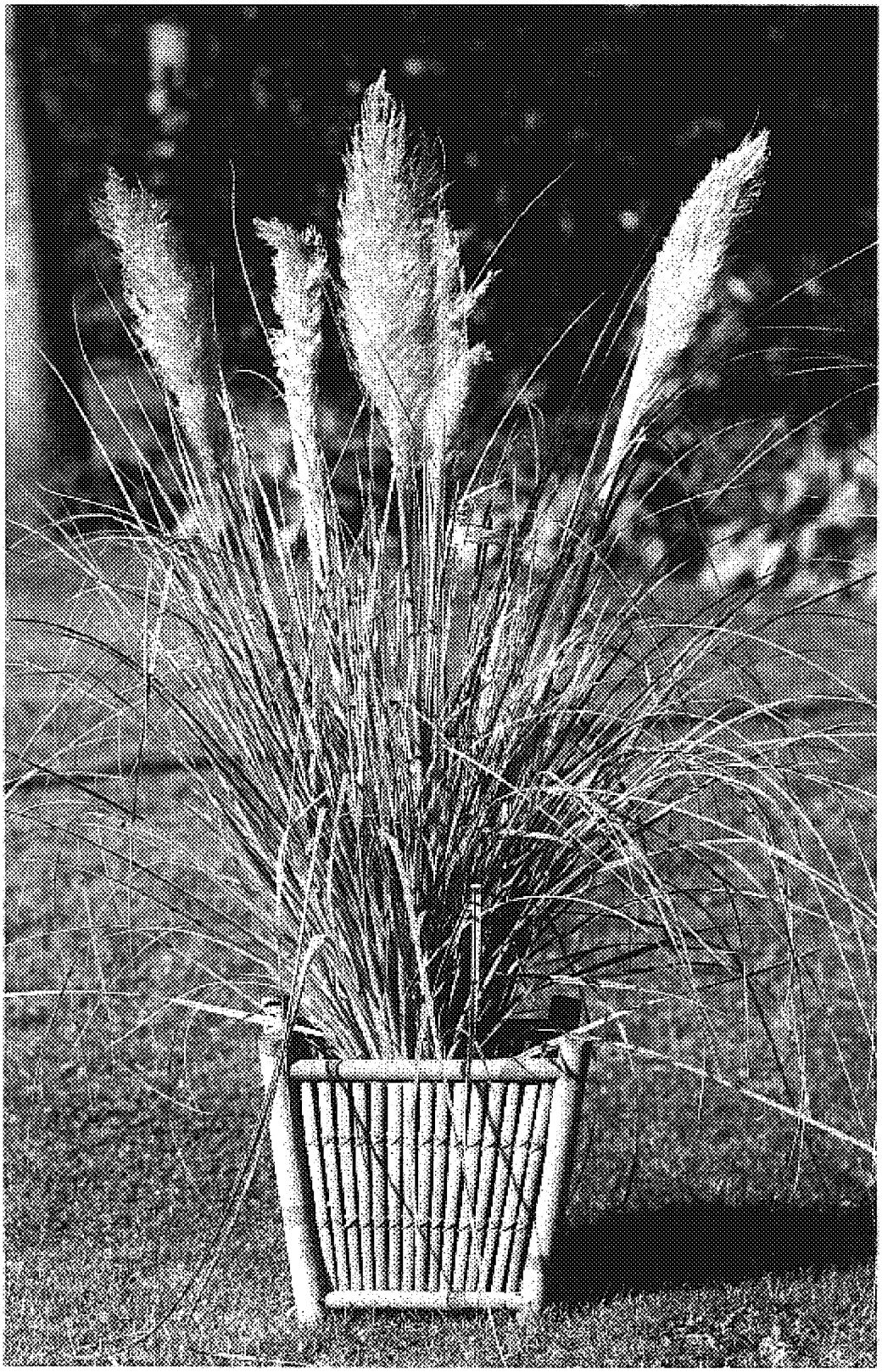
FIG. 1 is a photograph of the whole plant.
Figure 2:
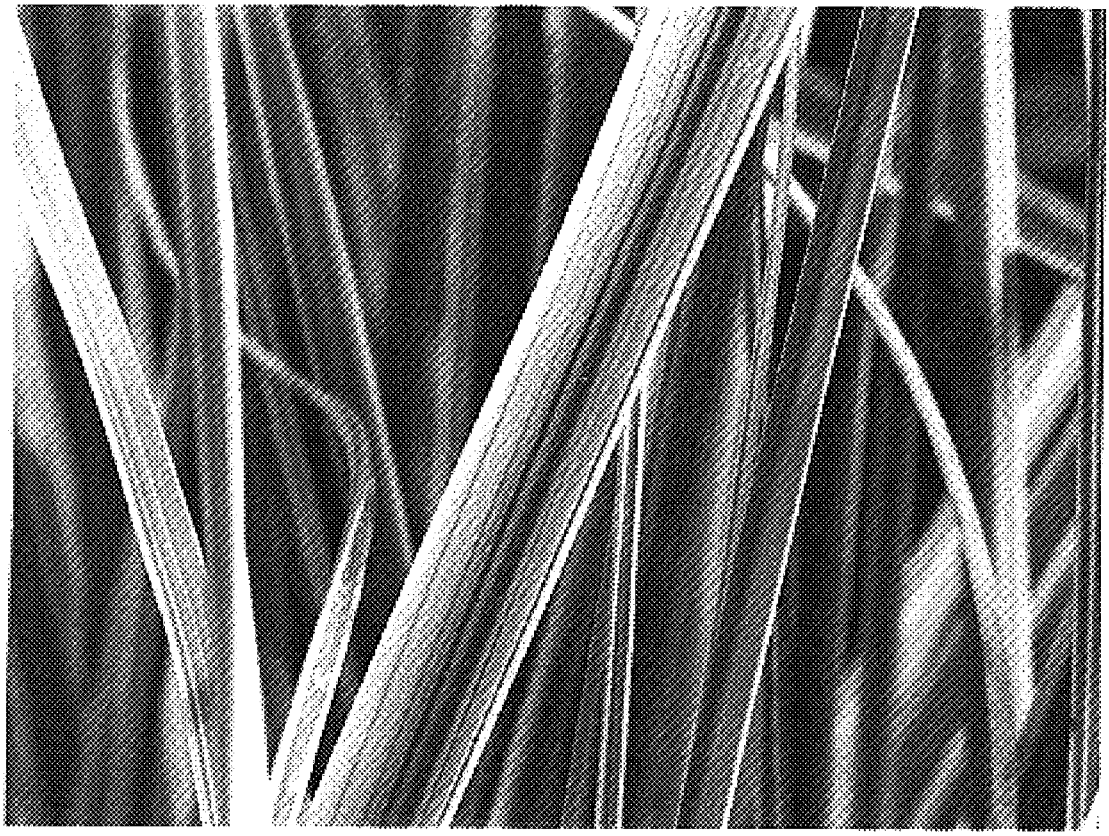
FIGS. 2–5 are photographs of the leaf blades of the new variety.
Figure 3:
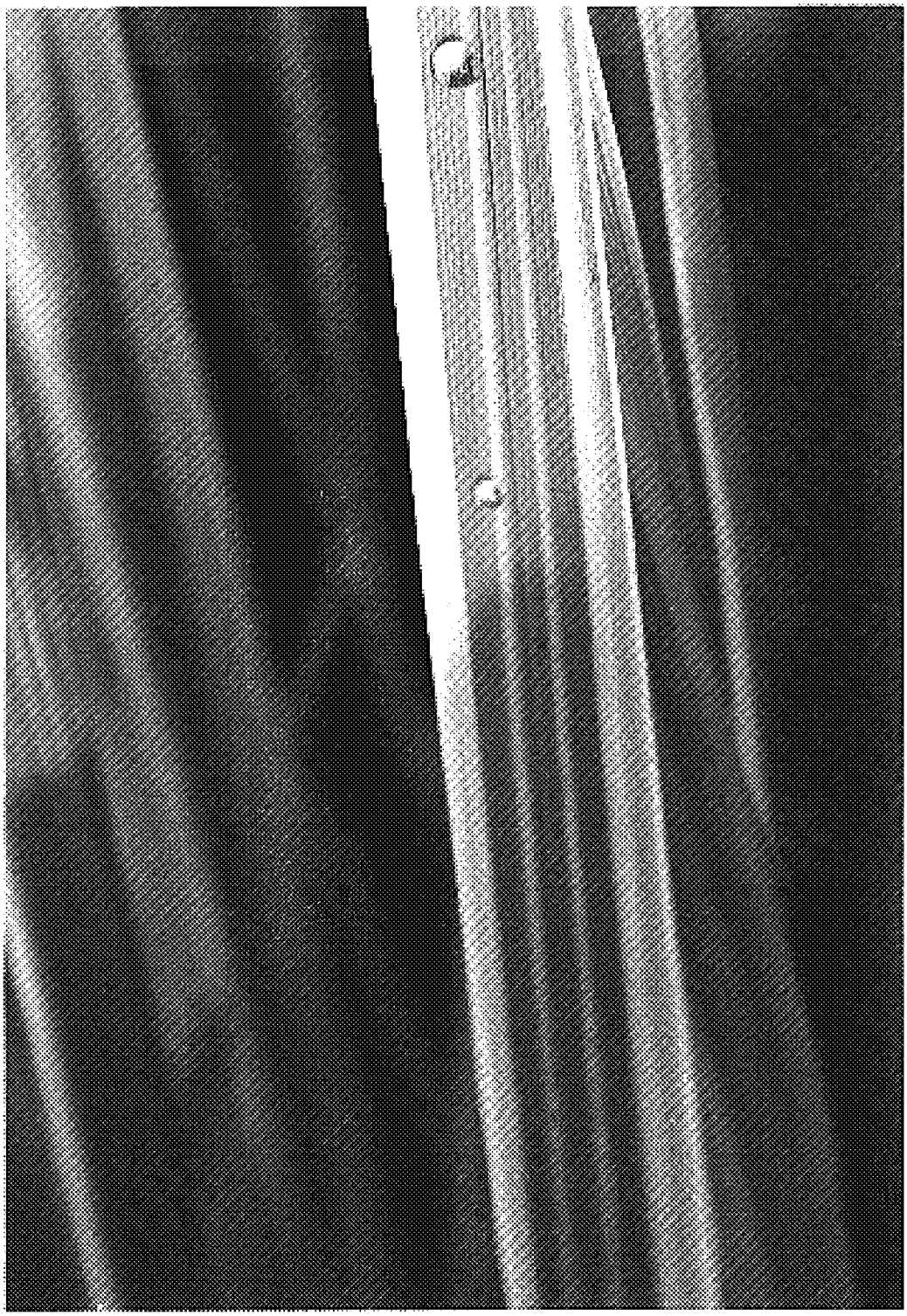
Figure 4:
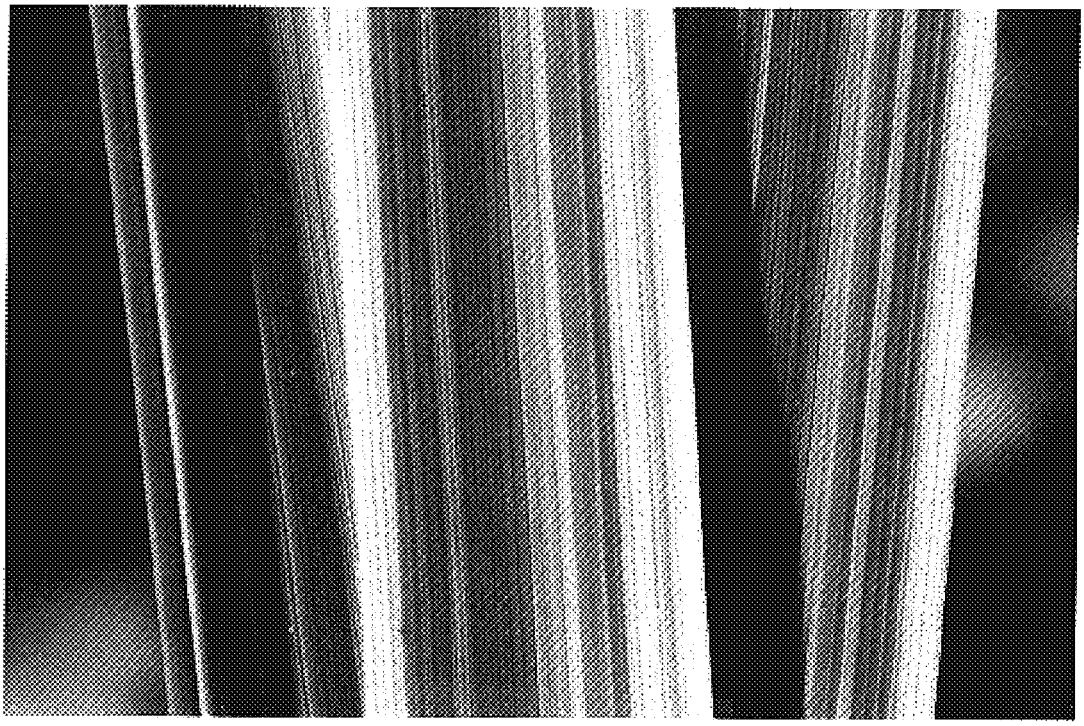
Figure 5:
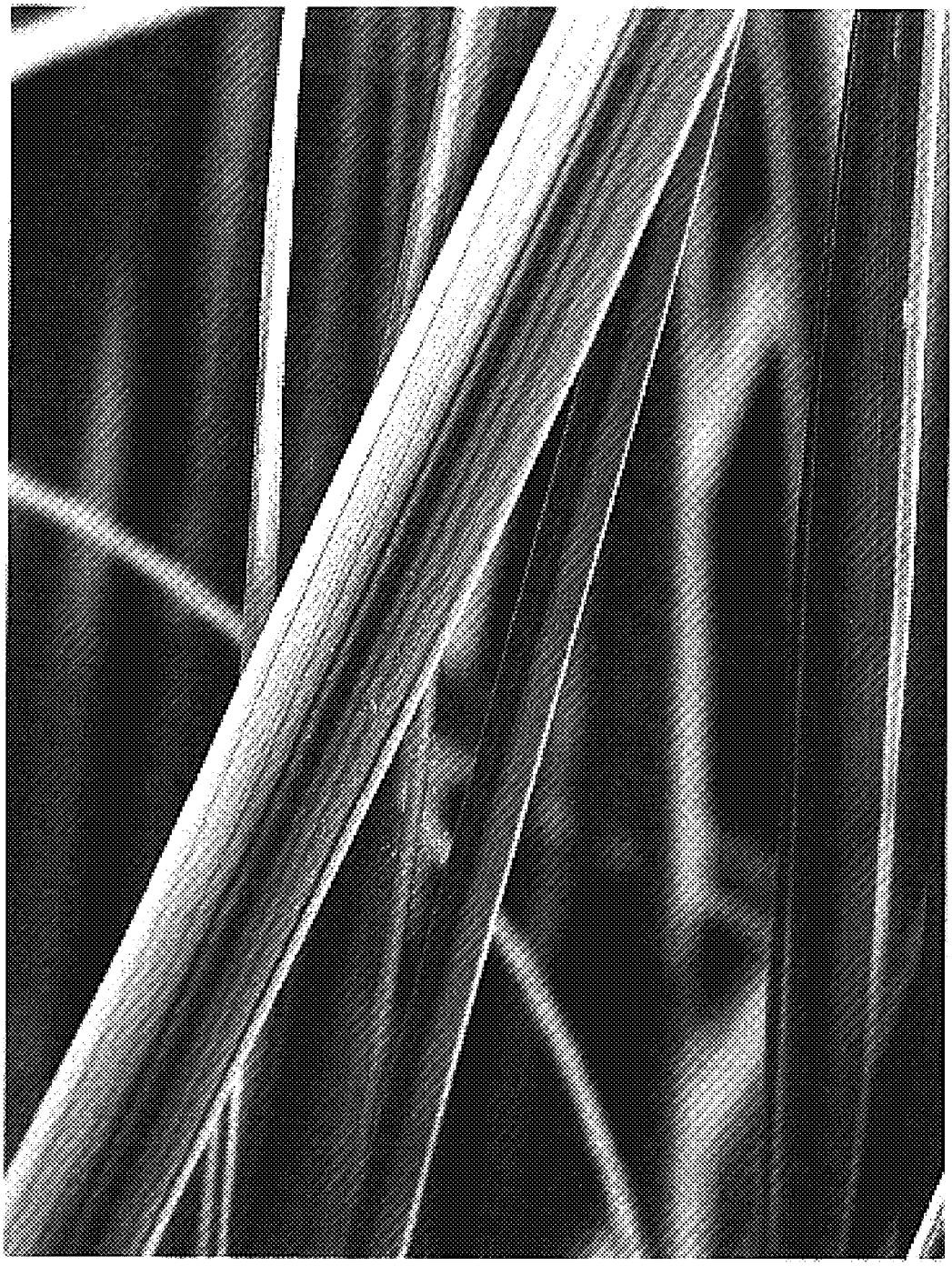

The submitted photographs were taken of a one-year old 'Amco' plant.

DESCRIPTION OF THE PLANT

The following detailed description sets forth characteristics of the new cultivar. The data which defines these characteristics were collected by asexual reproductions carried out in Germany. Plants for the description were grown in 25 cm pots in peat substrate and were one year old. The color readings were taken under natural, shadowed light. Color references are primarily to the 2001 R.H.S. Colour Chart of the Royal Horticultural Society of London.

PLANT

Height: 100 cm, but can reach up to 200 cm high when grown in open spaces.
Diameter: 110 cm.
Vigor: Compact.
Form: Erect and slightly spreading.
Roots:
- *Source.*—Rhizone.
- *Habit.*—Thick and fleshy.
- *Time to initiate roots.*—5 days at 15° C.
- *Time to develop roots.*—10 days at 15° C.

Time to produce a finished plant from a rooted cutting: 50 weeks in a 25 cm container.
Culms:
- *Diameter.*—0.8 cm.
- *Length.*—20–25 cm.
- *Color.*—146C and slightly pinkish 63D at the base.
- *Internode length.*—1.0–2.5 cm.
- *Texture.*—Smooth.
- *Pubescence.*—Very little present, but invisible and sharp.
- *Arrangement.*—Almost parallel from the base.

Plantlets:
- *Diameter.*—0.5 cm.
- *Average length.*—15 cm.
- *Internode length.*—1 cm.
- *Texture.*—Smooth.
- *Pubescence.*—Absence.
- *Color.*—146C.

Foliage:
- *Arrangement.*—Alternate.
- *Leaf blades.*—Shape: Linear. Number: 7–10 per culm. Width: 1 cm at the base, narrowing to 0.1 cm at the tip. Length: 40–60 cm. Shape of apex: Acuminate. Shape of base: Cuneate. Texture: Smooth, with invisible and sharp pubescence present. Aspect: Erect and arching. Margin type: Entire and white (chimeral pattern). Venation: Parallel. Pubescence: Upper surface: Very little present, invisible and partly sharp. Lower surface: Very little present, invisible and partly sharp.

*Color: Young leaf blade: Upper surface:* 138B with a white margin and 193C stripes in the middle. Lower surface: 146D with a white margin and 193C stripes in the middle. Mature leaf blade: Upper surface: 138A with a white margin and 193C stripes in the middle. Lower surface: 146C with a white margin and 193C stripes in the middle.

Ligules:

*Length.*—0.1 cm.
*Width.*—1.2–2.0 cm.
*Shape.*—Reduced and toothed.
*Color.*—193C.
*Pubescence.*—Present.
*Number.*—Two, one per side.
*Truncation.*—Toothed.

Sheaths:

*Length.*—Approximate 15 cm.
*Width.*—1.2–2.0 cm.
*Shape.*—Half-round and open.
*Color.*—138D, with a weak pink 63D at the base.

Petiole:

*Length.*—5–7 cm.
*Diameter.*—1.0 cm.
*Color.*—138D.

Veins:

*Venation type.*—Parallel, with a long acute top.
*Color.*—138C.

FLOWERS

Buds:

*When described.*—At 40 cm inflorescence length.
*Shape.*—Lanceolate.
*Diameter.*—0.1 cm.
*Length.*—0.2 cm.
*Color.*—138D.

Natural flowering season: September – November in Germany.

Flower:

*Type.*—Panicle.
*Corolla form.*—Zygormorphic.
*Fragrance.*—None present.
*Shape.*—Primary ascending contracted ramification.
*Number.*—Greater than 100 per panicle.
*Pedicle length.*—Approximately 0.5–1.5 cm.
*Peduncle length.*—100–110 cm.
*Petals.*—Number: 1 glume, approximately 50 lemma. Length: 1.0–1.5 cm. Width: 0.1 cm. Glume shape: Linear. Lemma shape: Fibril. Aspect: Upright, slightly outward. Margin: Smooth. Texture: Smooth. Color: When opening: 138D, both surfaces. Fully opened: 138C, both surfaces.
*Fragrance.*—None present.

REPRODUCTIVE ORGANS

Stamens: None present.

Pistils:

*Length.*—0.1 cm.
*Style.*—Length: 0.1 cm. Color: 157C.
*Stigma.*—Shape: Elongated. Color: 157C.

Seed/fruit production: sterile.

GENERAL

Cold tolerance: Protection in temperatures below −20° C. is suggested.

Disease resistance: Similar to other *Cortaderia* varieties known to the breeder.

Lasting quality: Flowers last on the variety from September to November.

I claim:

1. A new and distinct variety of *Cortaderia* plant substantially as herein shown and described.

* * * * *